United States Patent
Schumacher

(10) Patent No.: US 12,397,074 B2
(45) Date of Patent: Aug. 26, 2025

(54) DOOR HANDLE SANITIZING DEVICE

(71) Applicant: Germ Dome Industries LLC, Orchard Lake, MI (US)

(72) Inventor: Dean Schumacher, Orchard Lake, MI (US)

(73) Assignee: Germ Dome Industries LLC, Orchard Lake, MI (US)

( * ) Notice: Subject to any disclaimer, the term of this patent is extended or adjusted under 35 U.S.C. 154(b) by 441 days.

(21) Appl. No.: 18/080,014

(22) Filed: Dec. 13, 2022

(65) Prior Publication Data

US 2023/0248863 A1     Aug. 10, 2023

Related U.S. Application Data

(63) Continuation of application No. 16/932,221, filed on Jul. 17, 2020, now Pat. No. 11,524,085.

(51) Int. Cl.
   *A61L 2/10*     (2006.01)
   *A61L 2/24*     (2006.01)
   *G01P 13/00*     (2006.01)

(52) U.S. Cl.
CPC ............ *A61L 2/10* (2013.01); *A61L 2/24* (2013.01); *G01P 13/00* (2013.01); *A61L 2202/11* (2013.01); *A61L 2202/14* (2013.01)

(58) Field of Classification Search
CPC .......... A61L 2/10; A61L 2/24; A61L 2202/11; A61L 2202/14
See application file for complete search history.

(56) References Cited

U.S. PATENT DOCUMENTS

| | | | |
|---|---|---|---|
| 4,710,634 A | 12/1987 | Brookes | |
| 7,175,807 B1 | 2/2007 | Jones | |
| 7,989,779 B1 | 8/2011 | Ray et al. | |
| 9,649,398 B1 | 5/2017 | York | |
| 9,896,865 B2 * | 2/2018 | Samaras | E05B 1/0069 |
| 10,092,669 B2 | 10/2018 | Marshall | |
| D839,383 S * | 1/2019 | York | D23/208 |
| 10,309,124 B2 | 6/2019 | York | |
| 10,455,936 B2 | 10/2019 | McKnight et al. | |
| D895,764 S | 9/2020 | York | |
| D905,827 S * | 12/2020 | York | D23/254 |
| 10,994,040 B2 | 5/2021 | Kennedy et al. | |

(Continued)

FOREIGN PATENT DOCUMENTS

| | | |
|---|---|---|
| CN | 202672848 U | 1/2013 |
| DE | 102008063887 | 7/2010 |

(Continued)

OTHER PUBLICATIONS

Office Action from Chinese application No. 202180063493.1, dated Mar. 28, 2025, 10 pp.

(Continued)

*Primary Examiner* — Sean M Luck
(74) *Attorney, Agent, or Firm* — Greenberg Traurig, LLP

(57) ABSTRACT

A door handle sanitizing apparatus may include a posterior wall configured to be disposed anterior of and substantially parallel to a door surface and having an inner surface, an arch portion extending in an anterior direction from the posterior wall, the arch portion having an anterior end and an inner surface, a first sanitizing agent source disposed on the posterior wall, and a second sanitizing agent source disposed on the inner surface of the arch portion.

20 Claims, 9 Drawing Sheets

(56) References Cited

U.S. PATENT DOCUMENTS

| | | |
|---|---|---|
| 2005/0230638 A1 | 10/2005 | Ancona |
| 2006/0243762 A1 | 11/2006 | Sassoon |
| 2010/0051641 A1 | 3/2010 | Sassoon |
| 2011/0174992 A1 | 7/2011 | Sakita |
| 2012/0176241 A1 | 7/2012 | Pasch et al. |
| 2012/0305804 A1 | 12/2012 | Goldman |
| 2017/0246332 A1 | 8/2017 | Marshall |
| 2018/0085481 A1 | 3/2018 | Schumacher |
| 2018/0119447 A1 | 5/2018 | York |
| 2018/0339075 A1 | 11/2018 | Kennedy et al. |
| 2019/0117806 A1 | 4/2019 | Cahan et al. |
| 2019/0388572 A1 | 12/2019 | Cole et al. |
| 2020/0217102 A1 | 7/2020 | Gargash |

FOREIGN PATENT DOCUMENTS

| | | |
|---|---|---|
| DE | 102008063887 A1 | 7/2010 |
| KR | 200410373 Y1 | 5/2006 |
| KR | 20150000852 U | 2/2015 |
| KR | 20200016717 A | 2/2020 |
| WO | 2009056765 A2 | 5/2009 |

OTHER PUBLICATIONS

ISA/US, Inter'l Search Report and Written Opinion issued in Appl. No. PCT/US2021/041606, dated Oct. 21, 2021, 10 pgs.

U.S. Patent and Trademark Office, Non-Final Office Action issued in U.S. Appl. No. 17/032,187, dated Mar. 2, 2022, 7 pgs.

U.S. Patent and Trademark Office, Non-Final Office Action issued in U.S. Appl. No. 17/496,237, dated Feb. 9, 2023, 5 pgs.

Extended European Search Report from application No. 21843406.6, dated Sep. 23, 2024, 16 pp.

Final Office Action issued in U.S. Appl. No. 16/932,221, dated Mar. 22, 2022, 17 pgs.

\* cited by examiner

# DOOR HANDLE SANITIZING DEVICE

CROSS-REFERENCE TO RELATED APPLICATIONS

This application is a Continuation of U.S. patent application Ser. No. 16/932,221, now U.S. Pat. No. 11,524,085, entitled "DOOR HANDLE SANITIZING DEVICE," filed Jul. 17, 2020, the contents of which are incorporated herein for all purposes and in its entirety.

BACKGROUND a. Technical Field

The present disclosure relates to a device for sanitizing a point of contact. More specifically, this disclosure relates to a system and apparatus for sanitizing a door handle, door knob, or similar structure or device.

b. Background Art

Door handles, door knobs, other door opening devices, and other points of contact for large groups of people, such as automatic teller machines (ATMs) and elevator buttons or control panels, can be involved in the spread of communicable germs. In hospitals, germs communicated through points of contact can lead to increased patient sickness. In an office environment, germs communicated through points of contact can lead to sick employees and lost productivity. In public spaces, germs communicated through points of contact can lead to a sick populace and spread of disease.

The effect of germs spread through points of contact can be significantly reduced by sanitizing the surface of the point of contact periodically, such as after each use of the point of contact. There is therefore a need for a device to sanitize point-of-contact surfaces to eliminate one or more of the problems described above.

DETAILED DESCRIPTION OF THE INVENTION

It is known in the art that certain sanitizing agents may be used to sanitize objects and surfaces, such as door handles, door knobs, other door opening devices, automatic teller machines (ATMs), or elevator buttons and control panels. One type of sanitizing agent is electromagnetic energy of a particular frequency in the ultraviolet (UV) light spectrum. Ultraviolet light with a wavelength in the range of about 100 nanometers to about 280 nanometers (referred to herein as germicidal UV) is known to be deadly to bacteria and other micro-organisms, killing the micro-organisms, rendering them harmless, or eliminating their ability to reproduce. Germicidal UV with a wavelength of about 254 nanometers (a frequency of about 1.18 petahertz (PHz)) is known to be particularly effective. In one embodiment of the present invention, germicidal UV may be used as an effective agent for sanitizing doorknobs, other door opening devices, automatic teller machines (ATMs), elevator buttons and control panels, and other devices and apparatus that may be points of contact for a large volume of people, referred to herein as "points of contact." Similarly, as used herein, a "point-of-contact surface" refers to any surface of a point of contact. A device for sanitizing such point-of-contact surfaces may involve germicidal UV or other sanitizing agents.

Figure 1:
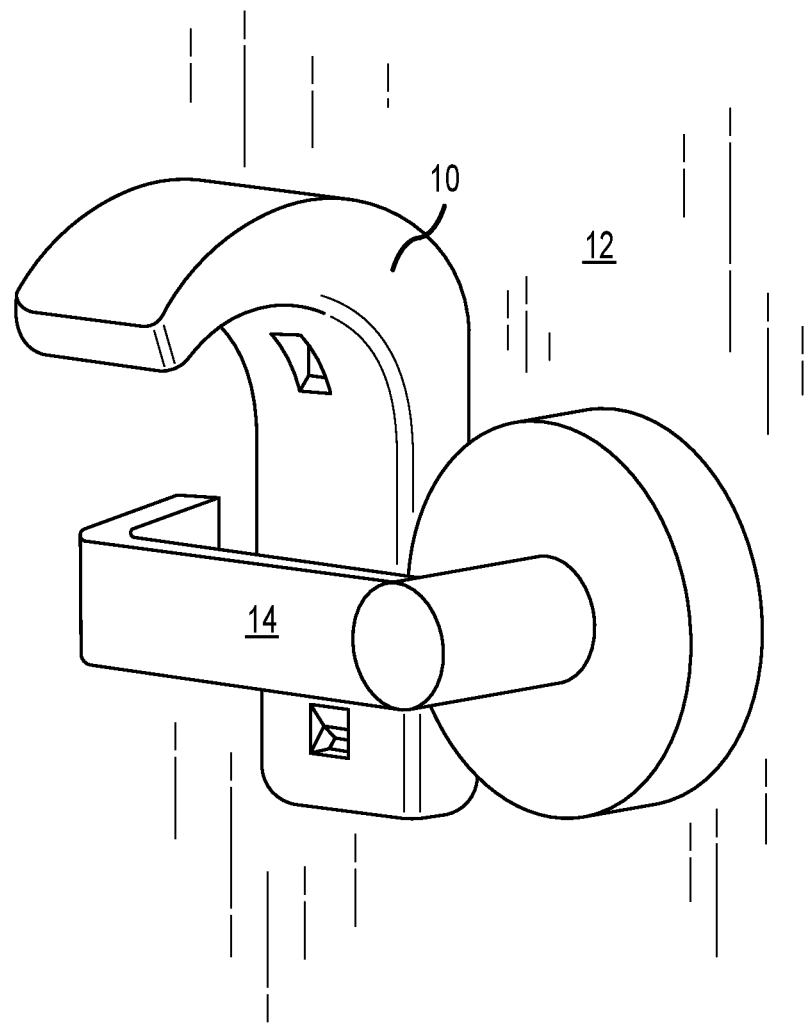
FIG. 1 is a perspective view of an example door handle sanitizing device coupled to a door adjacent to an example door handle.
Figure 2:
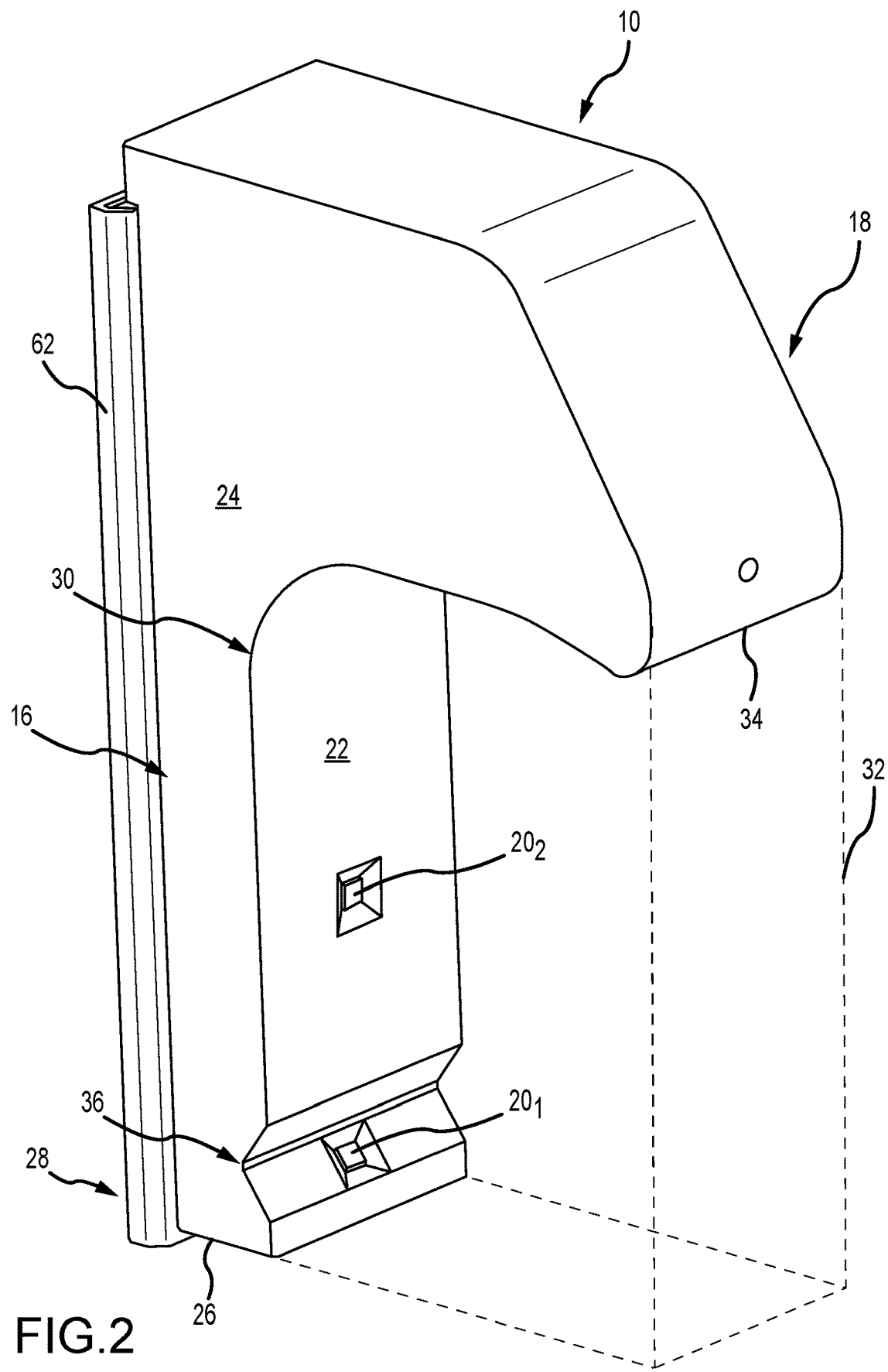
FIG. 2 is an upper perspective view of an example door handle sanitizing device.
Figure 3:
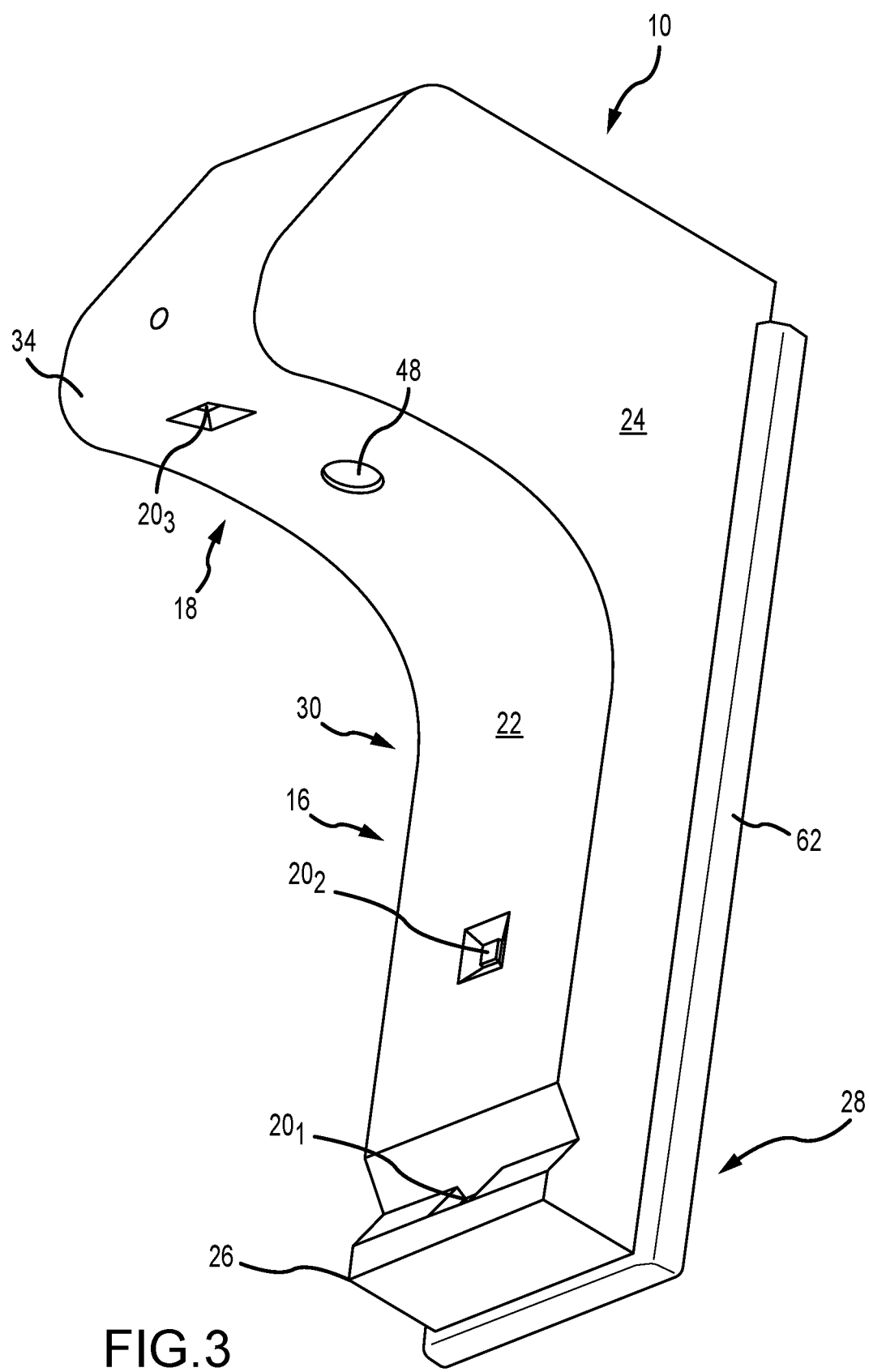
FIG. 3 is a lower perspective view of the example door handle sanitizing device of FIG. 2.
Figure 4:
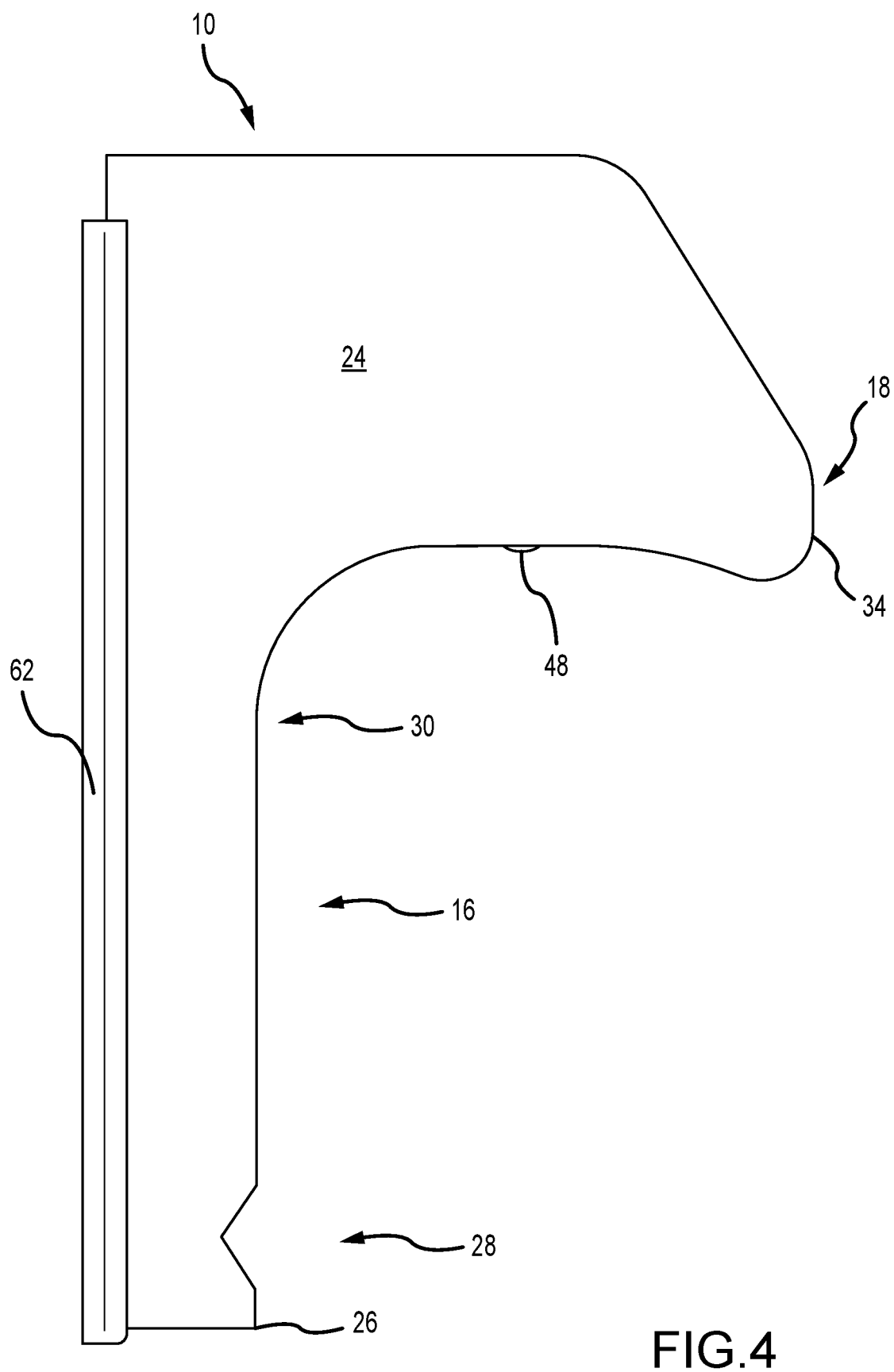
FIG. 4 is a left-side view of the example door handle sanitizing device of FIG. 2, the right-side being a mirror image.
Figure 5:
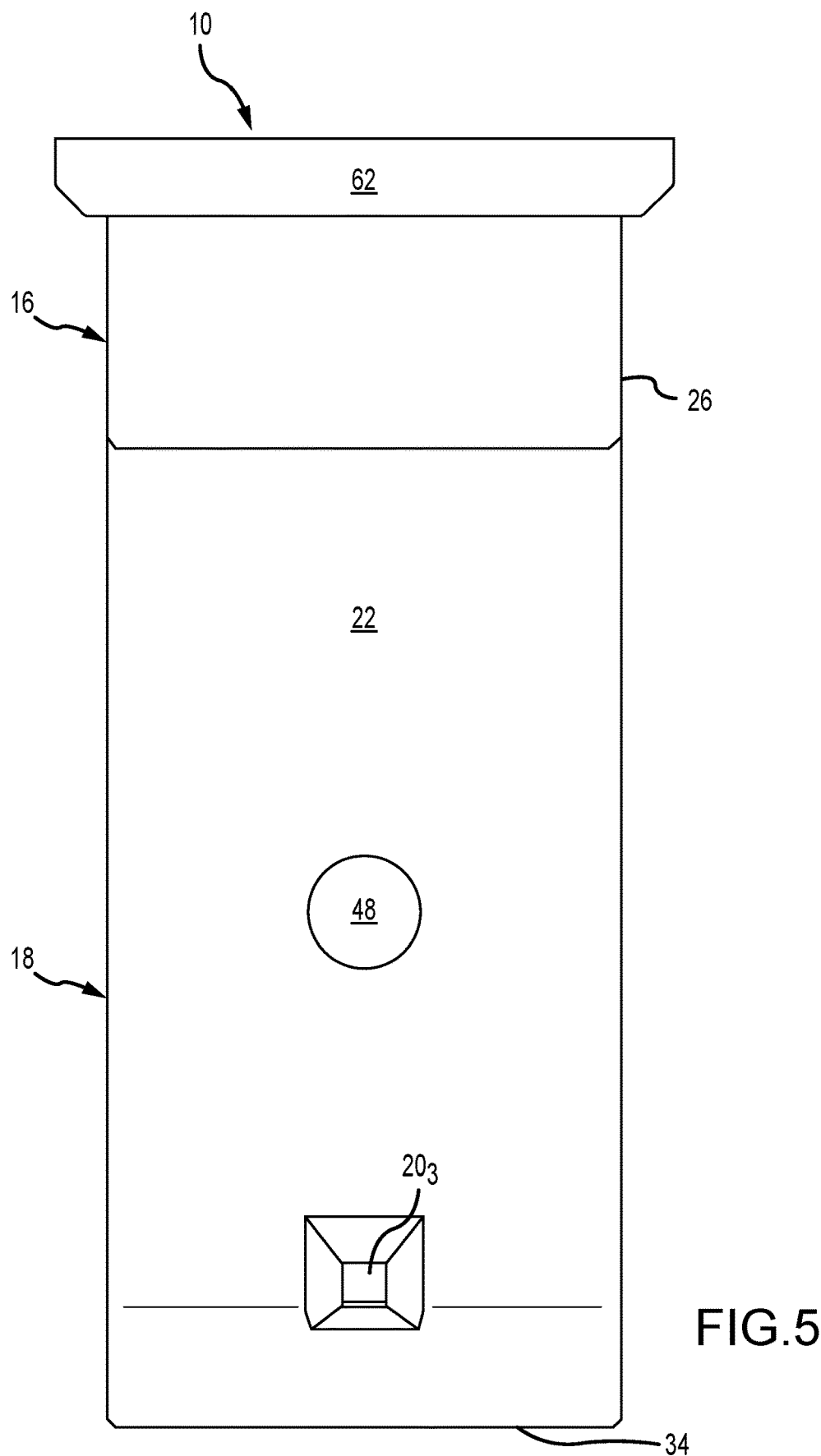
FIG. 5 is a bottom view of the example door handle sanitizing device of FIG. 2.

Referring now to the drawings wherein like reference numerals are used to identify identical components in the various views, FIG. 1 is a perspective view of an example door handle sanitizing device 10 disposed on an example door 12 adjacent to an example door handle 14 so as to sanitize the door handle 14.

FIGS. 2-5 are various views of the door handle sanitizing device 10 (which may be referred to herein as "the device 10" or "the apparatus 10") in isolation. Referring to FIGS. 1-6, the device 10 may include a linear portion 16 defining a posterior wall, an arched or curved portion 18, and one or more sources of a sanitizing agent 20 disposed on the linear portion 16 and/or arched portion 18 so as to sanitize the door handle 14 or other point of contact disposed adjacent to the device 10.

The linear portion 16 and arched portion 18 may share a common inner surface 22 and opposed sidewalls 24. The sidewalls 24 may be generally parallel to one another and generally transverse to the door 12, in some configurations (such as the configuration shown in FIG. 1). In other configurations, the device 10 may be coupled with a door 12 such that the sidewalls 24 are parallel with the door 12 and the inner surface 22 is transverse to the door 12.

The linear portion of the inner surface 22 may extend from a linear tip 26 at a bottom portion 28 of the device 10 to a transition portion 30. The arched portion 18 may extend in an anterior direction from the transition portion 30. The transition portion 30 may be at a top of the linear portion 16. The arched 18 portion may include a concave curve. Accordingly, in an embodiment, the inner surface 22 may form an approximately J-shaped surface (e.g., the transverse cross-section of the inner surface 22 may form a J-shape).

The inner surface 22 may define a projected three-dimensional volume 32 (shown in FIG. 2) that is bounded on its anterior side by an anterior-most point 34 of the arched portion 18 (and a downward plane from the anterior-most point 34 that is parallel with inner surface 22 at linear portion 16), on its upper side by the arched portion 18, on its lateral ends by planes normal to the lateral edges of the inner surface 22, and on its lower side by a normal plane from the linear tip 26. Accordingly, the volume 32 may extends anterior from the inner surface 22 of the linear portion 16, with the bottom of the volume 32 extending anterior from the linear tip 26. The device 10 may be positioned relative to a door handle 14 or other point of contact such that the door handle is disposed within or extends through the three-dimensional volume 32. Within the volume 32 may be projected two-dimensional areas (e.g., planes) that are bounded by the inner surface 22 on the posterior and upper sides and by normal planes from the linear tip 26 and anterior-most point 34. The device 10 may be positioned relative to a door handle 14 or other point of contact such that the door handle extends through one or more such two-dimensional planes. In some embodiments, the volume 32 may have a height of between three inches and nine inches, a width of between a half inch and three inches, and a depth (from anterior to posterior) of between one inch and six inches, for example.

The example device 10 includes three sanitizing agent sources $20_1$, $20_2$, $20_3$, which may be referred to collectively as sources 20 or individually as a source 20. More or fewer sanitizing agent sources 20 may be provided in different embodiments (e.g., two sources 20, four sources 20, and so on).

One or more of the sources 20 may be a source of ultraviolet (UV) light, such as germicidal UV. In some embodiments, one or more of the sources 20 may be one or more germicidal UV LEDs. In some embodiments, all of the sources 20 may be germicidal UV LEDs.

A first source $20_1$ may be disposed at a bottom portion 28 of the device and on the linear portion 16. The first source $20_1$ may be angled upward so as to project the sanitizing agent (e.g., germicidal UV light) in an anterior direction towards the arched portion 18. In some embodiments, the first source $20_1$ may be angled at between 15 and 75 degrees with respect to the primary plane of the inner surface 22 (and, thus, with respect to the door 12 when the device 10 is coupled to the door in the manner illustrated in FIG. 1). In some embodiments, the first source $20_1$ may be angled at between 30 and 60 degrees (i.e., configured to project light at such an angle) with respect to the primary plane of the inner surface 22 (that is, the primary plane within the linear portion 16). In some embodiments, the first source $20_1$ may be angled at about 45 degrees with respect to the primary plane of the inner surface 22. As used herein, the numerical values of angles of light projection of a source 20 refers to the center of the projection field of the source 20.

The linear portion 16 (e.g., the inner surface 22 thereof) may include a recess or notch 36 within which the first source $20_1$ may be disposed. The recess 36 may span the entire width of the inner surface 22 (e.g., from a first sidewall 24 to the opposite sidewall 24), in some embodiments, so as to provide the maximum light projection by the first source $20_1$ from within the recess 36. The first source $20_1$ may be disposed on a surface of the recess 36 having one of the above-noted angles with respect to the primary plane of the inner surface 22.

The second source $20_2$ may be disposed proximate a midpoint (e.g., between the linear tip 26 and the transition portion 30) of the linear portion 16, on the inner surface 22. The second source $20_2$ may be configured to project light in an anterior direction at a 90-degree angle with respect to the primary plane of the inner surface 22 (i.e., normal to the primary plane).

The third source $20_3$ may be disposed on the inner surface 22 of the arched portion 18. The third source $20_3$ may be configured to project light in a posterior direction towards the linear portion 16. That is, the third source may be angled to project sanitizing agent towards the door 12 when the device 10 is coupled to the door 12 as shown in FIG. 1.

The device 10 may further include a motion sensor 48 disposed on the inner surface 22 of the arched portion 18. The motion sensor 48 may thus be disposed under the arch of the arched portion 18. The motion sensor 48 may be configured to detect nearby motion, in response to which the sources 20 may be controlled, as will be described with respect to FIG. 9.

The motion sensor 48 may be positioned on the device 10 and have a desired sensitivity so as to detect motion within a desired distance of the device 10 (or within a desired distance of the point of contact sanitized by the device 10). In some embodiments, the motion sensor 48 may detect motion within 10 feet or less, 8 feet or less, 5 feet or less, 3 feet or less, 1 foot or less, or within another desired distance from the device 10. In an embodiment, the sensitivity of the motion sensor 48 may be selected according to the power of the sources 20. For example, in an embodiment in which the sources 20 are each germicidal UV LEDs having respective output intensities of two millijoules, the motion sensor 48 may be configured to detect motion within 1 foot of the device. In some embodiments, the effective range of the motion sensor 48 may be implemented in processing of the output of the motion sensor 48.

Figure 6:
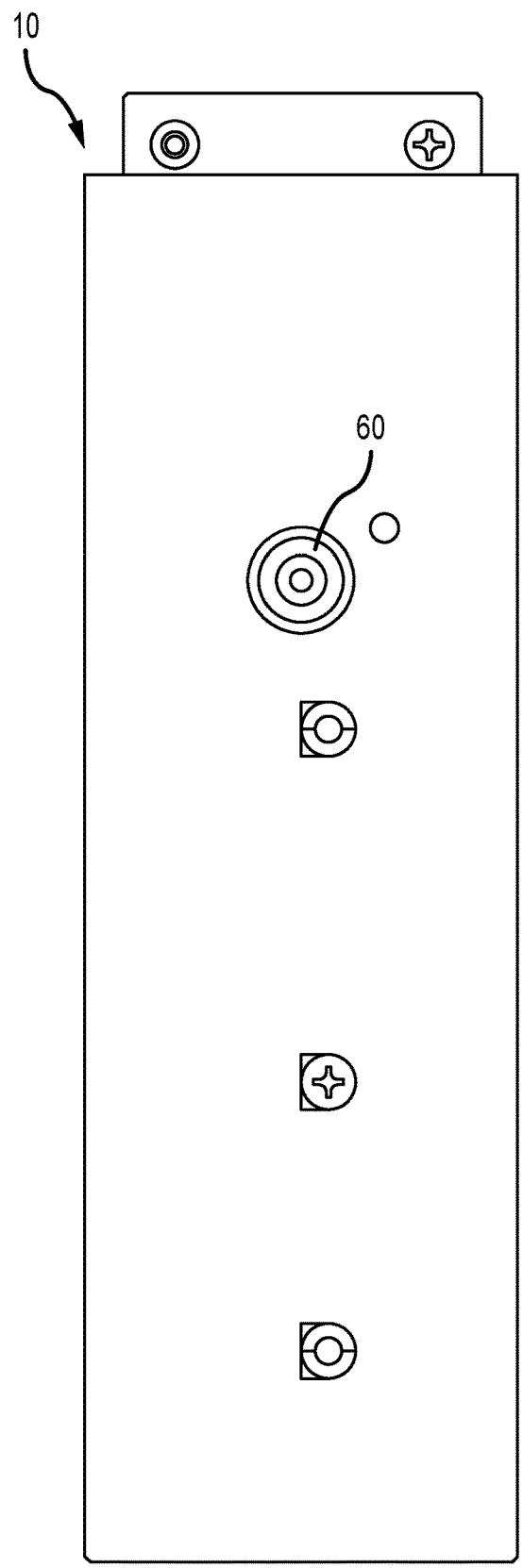
FIG. 6 is a rear view of the example door handle sanitizing device of FIG. 2, with the mounting plate omitted to illustrate the back of the body of the device.

FIG. 6 is a posterior view of the device 10, with the mounting bracket 62 omitted to show the back of the device 10. As shown in FIG. 6, the device 10 may include an electrical port 60 configured to receive a power input that may directly power the device 10 and/or charge a battery of the device 10, for example.

Figure 7:
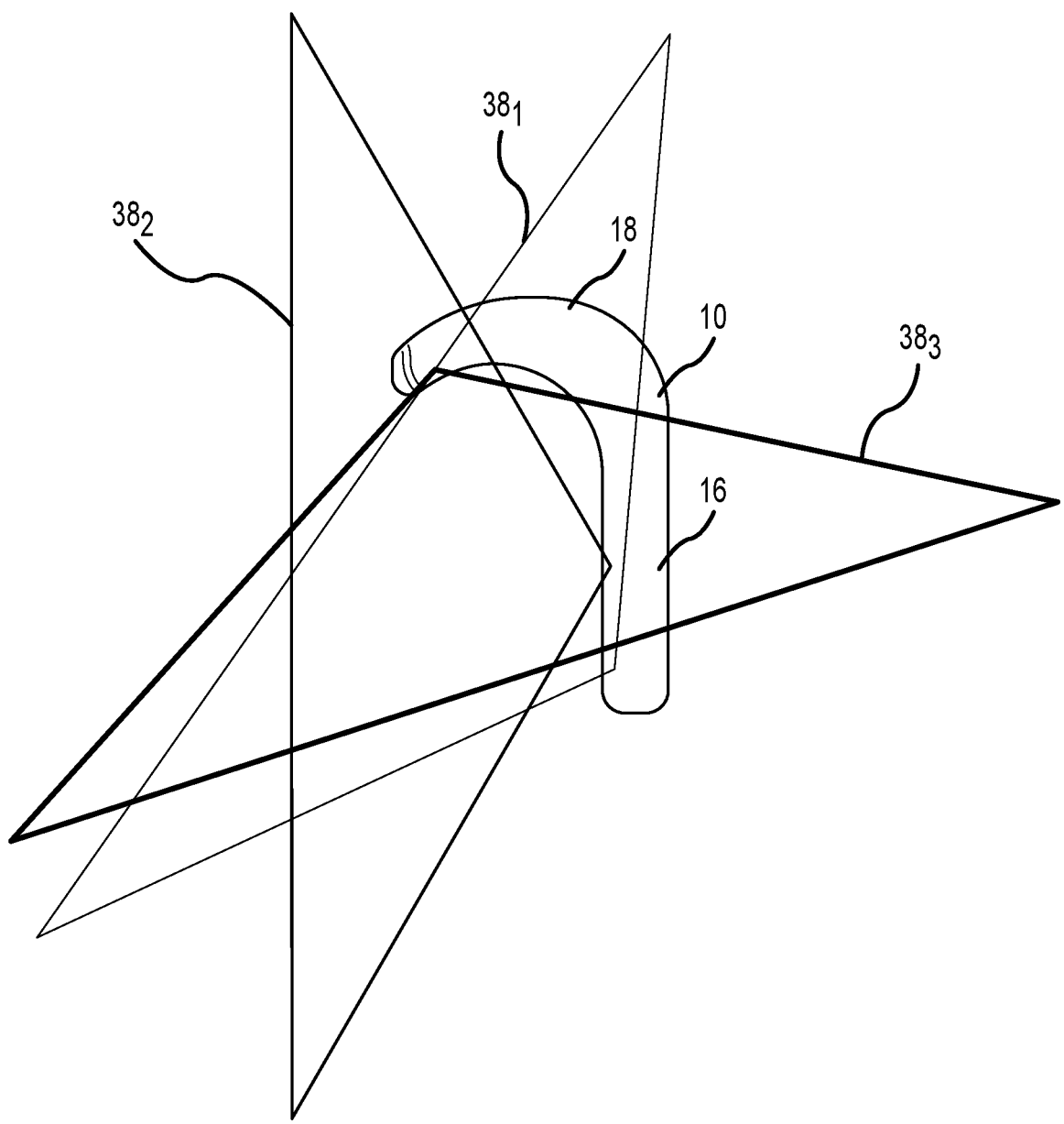
FIG. 7 is a side view of the example door handle sanitizing device, illustrating the projection field of the sanitizing agent of the device.

FIG. 7 is a diagrammatic side view illustrating example light projection fields and angles of the three sources $20_1$, $20_2$, $20_3$. Each source $20_1$, $20_2$, $20_3$ may have a respective projection field $38_1$, $38_2$, $38_3$ (which may be referred to individually as a projection field 38 or collectively as projection fields 38). One or more of the projection fields (e.g., each projection field) 38 may have a width and/or height of between 90 degrees and 150 degrees, in some embodiments. One or more of the projection fields (e.g., each projection field) 38 may have a width and/or height of between 100 degrees and 140 degrees, in some embodiments. One or more of the projection fields (e.g., each projection field) 38 may have a width and/or height of between 110 degrees and 130 degrees, in some embodiments. One or more of the projection fields (e.g., each projection field) 38 may have a width and/or height of about 120 degrees, in some embodiments.

As illustrated in FIG. 7, the sources $20_1$, $20_2$, $20_3$ may be arranged and configured so as to have overlapping fields 38 and/or to project sanitizing agent towards one another. For example, the field $38_1$ of the first source $20_1$ and the field $38_2$ of the second source $20_2$ may include the arched portion 18, and the field $38_3$ of the third source $20_3$ may include the linear portion 16. Further, the sources 20 may be arranged so that the fields 38 envelope the door handle 12 or other point of contact by striking the point of contact from different positions and angles.

Figure 8:
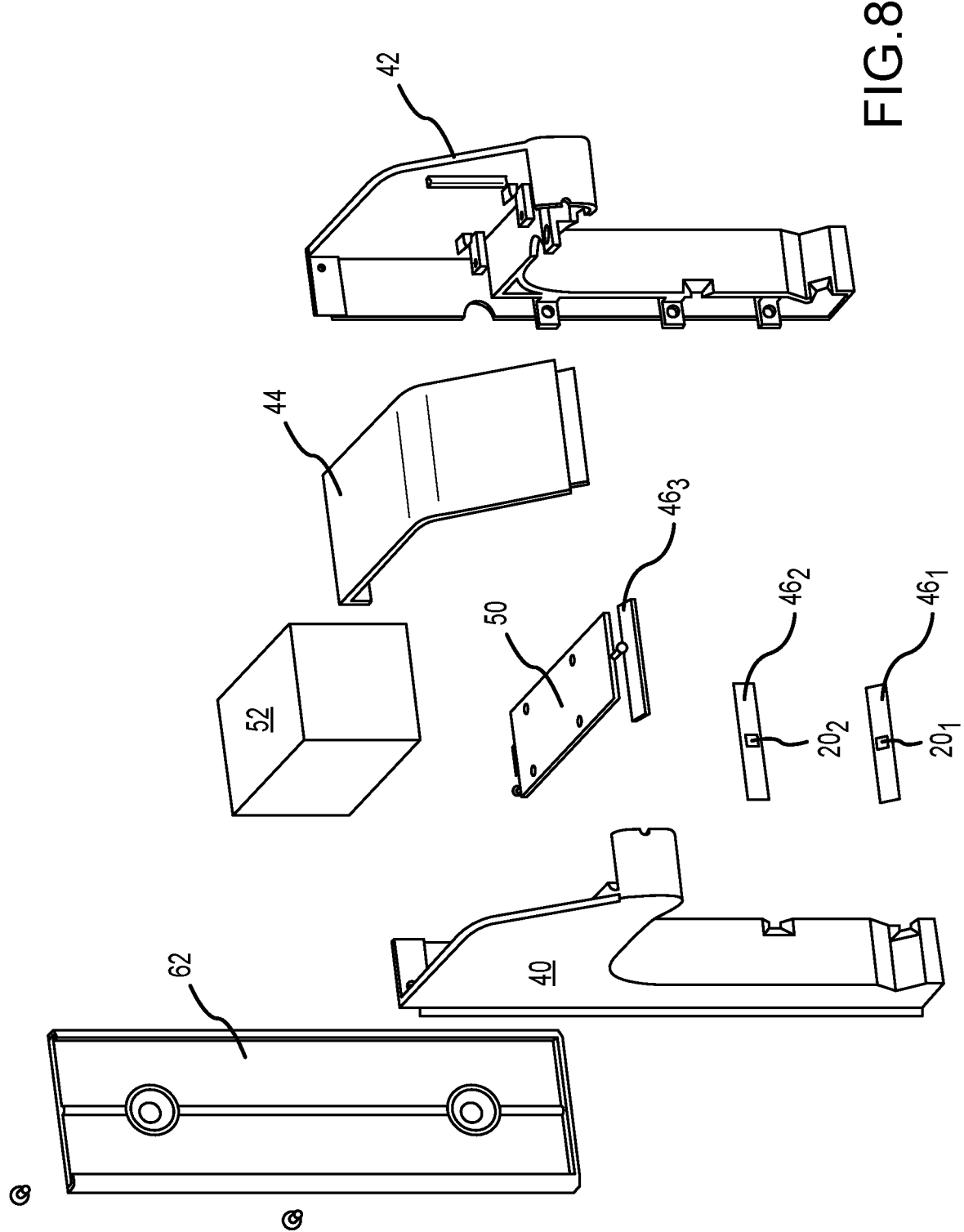
FIG. 8 is an exploded view of the example door handle sanitizing device of FIG. 2.

FIG. 8 is an exploded view of the device 10 illustrating an example construction of the device 10. The device 10 may include two lateral body portions 40, 42 and a cover 44 collectively defining the body of the device 10 and defining apertures through which the sources $20_1$, $20_2$, $20_3$ may project a sanitizing agent, such as germicidal ultraviolet light. The device may further include three LED chips $46_1$, $46_2$, $46_3$ on which the sources $20_1$, $20_2$, $20_3$ are respectively disposed, and a motion sensor chip 50 on which the motion sensor 48 (not designated in FIG. 8; designated in FIGS. 3, 4, and 5) is disposed. An electronics unit 52 may be provided that includes a power source, such as a battery, and an electronic control unit, which may comprise a combined processor and memory in some embodiments, for controlling the sources 20 in response to various stimuli (e.g., detected motion) and/or control strategies. The device 10 may further include a mounting bracket 62, which may be removably coupled from the body of the device 10 and which may be affixed to a door, wall, or other structure adjacent to a point of contact intended to be sanitized by the device 10. The mounting bracket 62 is also shown in FIGS. 2-5, but omitted in FIGS. 1, 6, and 7.

Figure 9:
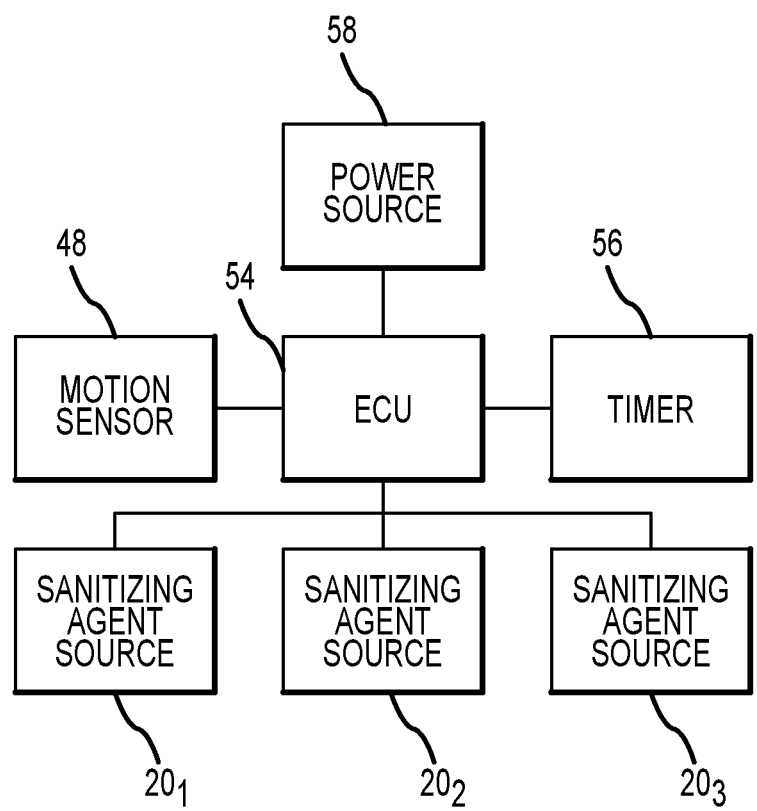
FIG. 9 is a block diagram of a portion of the example door handle sanitizing device of FIG. 2.

FIG. 9 is a block diagram of a portion of the device 10. The device portion may include an electronic control unit (ECU) 54 in electronic communication with the sources $20_1$, $20_2$, $20_3$, the motion sensor 48, a timer 56, and a power source 58. The ECU 54, sources 20, motion sensor 48, timer 56, and power source 58 may all be disposed in or on a body of the device 10, in some embodiments. The ECU 54 may include a non-transitory computer-readable memory storing instructions and a processor configured to execute the instructions on the memory to perform one or more operations or functions of the ECU 54. The timer 56 may be configured to track a time of day, a time elapsed since a previous sanitization or detected motion, or the time elapsed or remaining in a current sanitization cycle. In some embodiments, the timer 56 may be functionality of the ECU 54. The power source 58 may be one or more batteries, in some embodiments, that may be removable, replaceable, and/or rechargeable. In other embodiments, the power source may be a power supply configured to receive AC or DC input power from a persistent source, such as a wall outlet or other mains power supply.

The ECU 54 may be configured to activate or deactivate one or more sources 20 by instructing one or more of the sources 20 to activate or deactivate, by selectively providing power from the power source 58 to one or more of the sources 20, or otherwise. In some embodiments, the ECU 54 may be configured to activate and deactivate one or more sources 20 to effect a sanitization cycle of a predefined duration, such as 2 seconds, 3 seconds, 5 seconds, 10 seconds, 20 seconds, 30 seconds, 60 seconds, or another appropriate duration for sanitizing the door handle or other point of contact, during which sanitization cycle the sources 20 may output the sanitizing agent. The ECU 54 may be configured to execute a sanitization cycle on a predefined schedule, such as every 10 minutes, every 30 minutes, or every hour, in some embodiments. The sanitization cycle may be programmed depending on the time of day, in some embodiments, such as to be more frequent during business hours, for example. In some embodiment, the ECU 54 may receive an indication from the motion sensor 48 that motion was sensed and control a sanitization cycle responsive to the detected motion. For example, the ECU 54 may be configured to begin a sanitization cycle a set period of time after motion is sensed, such as 3 seconds, 5 seconds, 10 seconds, 15 seconds, or another period after motion was last detected. In another example, the ECU 54 may be configured to pause a sanitization cycle when motion is detected (e.g., so as to avoid exposing a user's hand, a nearby child's eyes, or other sensitive body part to germicidal UV or other sanitizing agent), and resume the sanitization cycle or beginning a new sanitization cycle a set period of time after the last motion was sensed, such as 3 seconds, 5 seconds, 10 seconds, 15 seconds, or another period of time. In some embodiments, a sanitization cycle may be executed in discrete segments, such as a first cycle segment of one of the above-noted periods of time, a pause of a predetermined duration, and a second cycle segment of one of or of above-noted periods of time.

In some embodiments, in addition to or instead of a timer 56 and/or a motion sensor 48, the device 10 may include a manual switch that may be connected to the ECU 54 to activate or deactivate a sanitization cycle. Such a switch may be disposed on a body of the device 10 or adjacent to the body, for example, and may be in wired or wireless communication with the ECU 54.

A device for sanitizing a point-of-contact surface, such as, for example, a door handle, other door opening device, ATM, or elevator buttons or control panel, as described herein has many advantages. The reduction of communicable germs in hospitals, where individuals may have weakened immune systems, may reduce loss of life and other illness resulting from transmitted germs. The reduction of communicable germs in the workplace and in schools may reduce lost work productivity and lost school days. The size and shape of the device can be tailored to a particular application, so the device need not unduly add to the bulk of the point-of-contact and can function with many different points of contact. The shapes and materials of the device may increase the efficiency and efficacy of the sources of a sanitizing agent—thereby lowering the necessary power consumption of the system and apparatus—by directing the sanitizing agent toward a location where the point-of-contact may be disposed. Additionally, because the sanitizing device may include one or more of, for example, a switch, timer, or motion sensor, the use and power consumption of the device can be scaled to the frequency that sanitization is necessary for a particular point of contact.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A door handle sanitizing apparatus comprising:
a posterior wall configured to be disposed anterior of and substantially parallel to a door surface and having an inner surface;
an arch portion extending in an anterior direction from the posterior wall, the arch portion having an anterior end and an inner surface;
a first sanitizing light source disposed on the posterior wall inner surface; and
a second sanitizing light source disposed on the inner surface of the arch portion, wherein a center of a light projection field of the second sanitizing light source intersects a plane comprising the posterior wall.

2. The door handle sanitizing apparatus of claim 1, wherein the first sanitizing light source or the second sanitizing agent source is a germicidal ultraviolet light source.

3. The door handle sanitizing apparatus of claim 1, wherein the first sanitizing light source or the second sanitizing agent source is an LED.

4. The door handle sanitizing apparatus of claim 1, wherein the first sanitizing light source is angled at between 30 degrees and 60 degrees with respect to the posterior wall.

5. The door handle sanitizing apparatus of claim 1, wherein the second sanitizing light source is angled to project the sanitizing agent towards the posterior wall.

6. The door handle sanitizing apparatus of claim 1, further comprising a motion sensor disposed under the arch portion, wherein the apparatus is configured to deactivate the first and second sanitizing light sources responsive to the motion sensor detecting motion.

7. The door handle sanitizing apparatus of claim 6, further comprising an electronic controller in electronic communication with the motion sensor, wherein the controller is configured to:
    instruct the first and second sanitizing light sources to begin a sanitization cycle;
    receive an indication from the motion sensor that the motion sensor has detected motion;
    in response to the indication, instruct the first and second sanitizing light sources to pause the sanitization cycle; and
    instruct the first and second sanitizing light sources to resume the sanitization cycle.

8. The door handle sanitizing apparatus of claim 7, wherein the controller is further configured to instruct the first and second sanitizing light sources to resume the sanitization cycle in response to the motion sensor not detecting motion for a predetermined period of time.

9. A door handle sanitizing apparatus comprising:
    an inner surface comprising:
        a first, linear portion disposed generally parallel to a door and anterior to the door when the apparatus is affixed to the door, wherein the first portion extends from a transition portion to a linear tip; and
        a second, curved portion that projects in an anterior direction and curves away from the transition portion of the first portion to an anterior tip;
    wherein the inner surface defines a projected two-dimensional area that is perpendicular to the door and extends along the inner surface, anterior from the linear tip, and down from the anterior tip;
    a first sanitizing agent source disposed on the first portion; and
    a second sanitizing agent source disposed on the second portion;
    wherein the apparatus is configured to receive and sanitize a door handle extending through the projected two-dimensional area.

10. The door handle sanitizing apparatus of claim 9, further comprising:
    two opposed sidewalls that are generally parallel to each other and generally transverse to the door when the apparatus is affixed to the door;
    wherein the inner surface extends between the two sidewalls.

11. The door handle sanitizing apparatus of claim 9, wherein a transverse cross-sectional shape of the inner surface is a J-shape.

12. The door handle sanitizing apparatus of claim 9, wherein the first sanitizing agent source or the second sanitizing agent source is a germicidal ultraviolet light source.

13. The door handle sanitizing apparatus of claim 9, wherein the first sanitizing ag agent source or the second sanitizing agent source is an LED.

14. The door handle sanitizing apparatus of claim 9, wherein the second sanitizing agent is angled at between 30 degrees and 60 degrees with respect to the first portion.

15. The door handle sanitizing apparatus of claim 9, wherein the second sanitizing agent source is angled to project the sanitizing agent towards the first portion.

16. A door handle sanitizing apparatus comprising:
    an inner surface comprising:
        a posterior portion disposed generally parallel to a door and anterior to the door when the apparatus is affixed to the door, wherein the posterior portion extends from a transition portion to a linear tip; and
        an arched portion that projects in an anterior direction and curves away from the transition portion of the first portion to an anterior tip,
        wherein the inner surface defines a projected two-dimensional area that is perpendicular to the door and extends along the inner surface, anterior from the linear tip, and down from the anterior tip;
    a first sanitizing agent source disposed on the posterior portion; and
    a second sanitizing agent source disposed on the arched portion;
    wherein a transverse cross-sectional shape of the inner surface is a J-shape.

17. The door handle sanitizing apparatus of claim 16, wherein the apparatus is configured to receive and sanitize a door handle extending through the projected two-dimensional area.

18. The door handle sanitizing apparatus of claim 16, wherein the first sanitizing agent source or the second sanitizing agent source is a germicidal ultraviolet light source.

19. The door handle sanitizing apparatus of claim 16, further comprising a motion sensor disposed under the arch portion, wherein the apparatus is configured to deactivate the first and second sanitizing agent sources responsive to the motion sensor detecting motion.

20. The door handle sanitizing apparatus of claim 19, further comprising an electronic controller in electronic communication with the motion sensor, wherein the controller is configured to:
    instruct the first and second sanitizing agent sources to begin a sanitization cycle;
    receive an indication from the motion sensor that the motion sensor has detected motion;
    in response to the indication, instruct the first and second sanitizing agent sources to pause the sanitization cycle; and
    instruct the first and second sanitizing agent sources to resume the sanitization cycle.

\* \* \* \* \*